(12) United States Patent
Price et al.

(10) Patent No.: US 9,213,802 B2
(45) Date of Patent: Dec. 15, 2015

(54) UPDATABILITY OF STRUCTURED BLOOD GLUCOSE TESTS PERFORMED ON HANDHELD DIABETES MANAGEMENT DEVICES

(75) Inventors: John F. Price, McCordsville, IN (US); Paul J. Galley, Cumberland, IN (US)

(73) Assignee: Roche Diabetes Care, Inc., Indianapolis, IN (US)

( * ) Notice: Subject to any disclaimer, the term of this patent is extended or adjusted under 35 U.S.C. 154(b) by 1089 days.

(21) Appl. No.: 12/905,425

(22) Filed: Oct. 15, 2010

(65) Prior Publication Data

US 2012/0095309 A1  Apr. 19, 2012

(51) Int. Cl.
*G06F 19/00* (2011.01)
*A61B 5/145* (2006.01)

(52) U.S. Cl.
CPC ......... *G06F 19/3462* (2013.01); *A61B 5/14532* (2013.01); *G06F 19/323* (2013.01); *G06F 19/325* (2013.01)

(58) Field of Classification Search
CPC ............ A61B 5/14532; G06F 19/3406; G06F 19/3412
USPC .............................. 600/345, 347, 365; 422/50
See application file for complete search history.

(56) References Cited

U.S. PATENT DOCUMENTS

2002/0147390 A1* 10/2002 Markis et al. .................. 600/301
2007/0083916 A1*  4/2007 Coyle .............................. 726/4
2010/0069730 A1   3/2010 Bergstrom et al.
2010/0212675 A1   8/2010 Walling et al.
2010/0218132 A1*  8/2010 Soni et al. ..................... 715/771

OTHER PUBLICATIONS

U.S. Department of Health and Human Services Food and Drug Administration. "Guidance for the Content of Premarket Submissions for Software Contained in Medical Devices". May 11, 2005.*
U.S. Appl. No. 61/393,519, Galley et al.
U.S. Appl. No. 12/905,417, Galley et al.
U.S. Appl. No. 12/905,420, Galley et al.
U.S. Appl. No. 12/621,836, Stewart et al.
Smiths Medical MD, Inc., Deltec Cozmo®, Fine Tuning Your Deltec Cozmo® Insulin Pump Settings, Overnight Basal Rate Test Instructions, 2 pp, Date Unknown.
Smiths Medical MD, Inc., Deltec Cozmo®, User Manual, Deltec Cozmo® Insulin Pump, 245 pp, Date Unknown.

\* cited by examiner

*Primary Examiner* — Michael D'Angelo
*Assistant Examiner* — Christian Jang
(74) *Attorney, Agent, or Firm* — Harness, Dickey

(57) ABSTRACT

A method of improving updatability of entry, adherence, and exit criteria stored in memory of a handheld diabetes management device, the method includes: providing the handheld diabetes management device with a blood glucose (bG) measurement engine that measures a bG level in a sample of blood of a user and that generates sample data indicative of the bG level; providing the handheld diabetes management device with the memory and a touchscreen display; providing the handheld diabetes management device with a processor module that is in communication with the bG measurement engine, the touchscreen display, and the memory; storing firmware that is executable by the processor module for performing operations to carry out a structured bG test in a non-modifiable portion of the memory; and storing the entry, adherence, and exit criteria in a modifiable portion of the memory.

9 Claims, 6 Drawing Sheets

UPDATABILITY OF STRUCTURED BLOOD GLUCOSE TESTS PERFORMED ON HANDHELD DIABETES MANAGEMENT DEVICES

FIELD

The present disclosure relates to handheld medical devices and more particularly to handheld blood glucose (bG) management devices.

BACKGROUND

The background description provided herein is for the purpose of generally presenting the context of the disclosure. Work of the presently named inventors, to the extent it is described in this background section, as well as aspects of the description that cannot otherwise qualify as prior art at the time of filing, are neither expressly nor impliedly admitted as prior art against the present disclosure.

Diabetes mellitus, often referred to as diabetes, is a chronic condition in which a person has elevated blood glucose levels that result from defects in the body's ability to produce and/or use insulin. There are three main types of diabetes. Type 1 diabetes usually strikes children and young adults, and can be autoimmune, genetic, and/or environmental. Type 2 diabetes accounts for 90-95% of diabetes cases and is linked to obesity and physical inactivity. Gestational diabetes is a form of glucose intolerance diagnosed during pregnancy and usually resolves spontaneously after delivery.

In 2009, according to the World Health Organization, at least 220 million people worldwide suffer from diabetes. In 2005, an estimated 1.1 million people died from diabetes. The incidence of diabetes is increasing rapidly, and it is estimated that between 2005 and 2030, the number of deaths from diabetes will double. In the United States, nearly 24 million Americans have diabetes with an estimated 25 percent of seniors age 60 and older being affected. The Centers for Disease Control and Prevention forecast that 1 in 3 Americans born after 2000 will develop diabetes during their lifetime. The National Diabetes Information Clearinghouse estimates that diabetes costs $132 billion in the United States alone every year. Without treatment, diabetes can lead to severe complications such as heart disease, stroke, blindness, kidney failure, amputations, and death related to pneumonia and flu.

Management of diabetes is complex because the level of blood glucose entering the bloodstream is dynamic. Variation of insulin in the bloodstream that controls the transport of glucose out of the bloodstream also complicates diabetes management. Blood glucose levels are sensitive to diet and exercise, but also can be affected by sleep, stress, smoking, travel, illness, menses, and other psychological and lifestyle factors that are unique to each patient. The dynamic nature of blood glucose and insulin, and all other factors affecting blood glucose, often require a person with diabetes to forecast blood glucose levels. Administration of insulin and/or oral medications can be regulated and timed to maintain blood glucose levels within an appropriate range at all times.

Management of diabetes is often highly intrusive because of the need to consistently obtain reliable diagnostic information, follow prescribed therapy, and manage lifestyle on a daily basis. Diagnostic information, such blood glucose level, can be obtained from a capillary blood sample with a lancing device and a test strip. The blood glucose level is measured via the test strip using a handheld blood glucose meter. Interstitial glucose levels can be obtained from a continuous glucose sensor worn on the body.

A therapy regimen for a patient can be established based on one or more of the patient's blood glucose levels. The therapy regimen can include administration of insulin and/or oral medication. Insulin can be administered with a syringe, an ambulatory infusion pump, or a combination of both. With insulin therapy, determining the amount of insulin to inject at a given time can require forecasting meal composition (e.g., of fat, carbohydrates, and proteins). Determining the amount of insulin to inject at a given time can also require consideration of the effects of exercise and physiologic state. The patient's management of lifestyle factors such as body weight, diet, and exercise can significantly influence the type and effectiveness of therapy.

Management of diabetes involves large amounts of diagnostic data and prescriptive data that are acquired from medical devices, personal health care devices, patient recorded information, health care professional tests results, prescribed medications and recorded information. Medical devices including self-monitoring bG meters, continuous glucose monitors, ambulatory insulin infusion pumps, diabetes analysis software, and diabetes device configuration software each of which generates or manages or both large amounts of diagnostic and prescriptive data. Personal health care devices can include weights, scales, and blood pressure cuffs. Patient recorded information can include information relating to meals, exercise, and lifestyle. Health care professional biomarker data can include HbAlC, cholesterol, triglycerides, and glucose tolerance. Health care professional recorded information can include therapy and other patient-specific information.

At the present time, a patient with diabetes can be asked by a health care professional to conduct, for example, a three day blood glucose (bG) test. A three day profile bG structured test involves the patient checking his or her bG level several times during each day for three days and hand writing the bG measurements in a chart. Preferably, the three day profile bG structured test is performed with the patient checking his or her bG level at seven different times on each of the three days and recording the seven different measurements each day. The seven different times at which a patient should measure and record his or her bG level are: 1) pre-breakfast; 2) post-breakfast; 3) pre-lunch; 4) post-lunch; 5) pre-dinner; 6) post-dinner; and 7) bedtime. The patient should consume breakfast between measurements 1 and 2, lunch between measurements 3 and 4, and dinner between measurements 5 and 6. Based on the results of the three day profile bG structured test, a health care professional can determine or adjust an insulin therapy for the patient. There is a need for a handheld patient device to aggregate, manipulate, manage, present, and communicate diagnostic data and prescriptive data from medical devices, personal health care devices, patient recorded information, biomarker information and recorded information in an efficient manner. This would enable the patient to improve his or her care and health, to lead a full life, and to reduce the risk of complications from diabetes.

SUMMARY

A handheld diabetes management device having improved updatability of entry, adherence, and exit criteria, includes: a blood glucose (bG) management engine, memory, a display, and a processor module. The bG measurement engine that measures a bG level in a sample of blood of a user and that generates sample data indicative of the bG level. The processor module is in communication with the bG measurement engine, the display, and the memory. The processor module selectively executes firmware stored in a non-modifiable portion of the memory for performing operations to carry out a structured bG test; selectively retrieves entry, adherence, and exit criteria stored in a modifiable portion of the memory for individual bG samples expected to be input for the structured bG test; selectively retrieves entry, adherence, and exit criteria stored in the modifiable portion of the memory for bG sample groups expected for the structured bG test; and retrieves entry, adherence criteria, and exit criteria from the modifiable portion of the memory for the structured bG test.

A computer readable storage medium for a handheld blood glucose (bG) management device that measures a user's bG level and that includes a touchscreen display, the computer readable storage medium comprising a modifiable portion and a non-modifiable portion. The modifiable portion includes adherence, exit, and entry criteria for performing a structured bG test are stored. The non-modifiable portion includes firmware that, when executed by a processor of the handheld diabetes management device, causes the processor to perform the structured bG test involving obtaining measurements of the user's bG level according to a predefined schedule and selectively retrieving the adherence, exit, and entry criteria from the modifiable portion.

A method of improving updatability of entry, adherence, and exit criteria stored in memory of a handheld diabetes management device, the method includes: providing the handheld diabetes management device with a blood glucose (bG) measurement engine that measures a bG level in a sample of blood of a user and that generates sample data indicative of the bG level; providing the handheld diabetes management device with the memory and a touchscreen display; providing the handheld diabetes management device with a processor module that is in communication with the bG measurement engine, the touchscreen display, and the memory; storing firmware that is executable by the processor module for performing operations to carry out a structured bG test in a non-modifiable portion of the memory; and storing the entry, adherence, and exit criteria in a modifiable portion of the memory.

Further areas of applicability of the present disclosure will become apparent from the detailed description provided hereinafter. It should be understood that the detailed description and specific examples are intended for purposes of illustration only and are not intended to limit the scope of the disclosure.

BRIEF DESCRIPTION OF THE DRAWINGS

The present disclosure will become more fully understood from the detailed description and the accompanying drawings, wherein.

DETAILED DESCRIPTION

Figure 1:
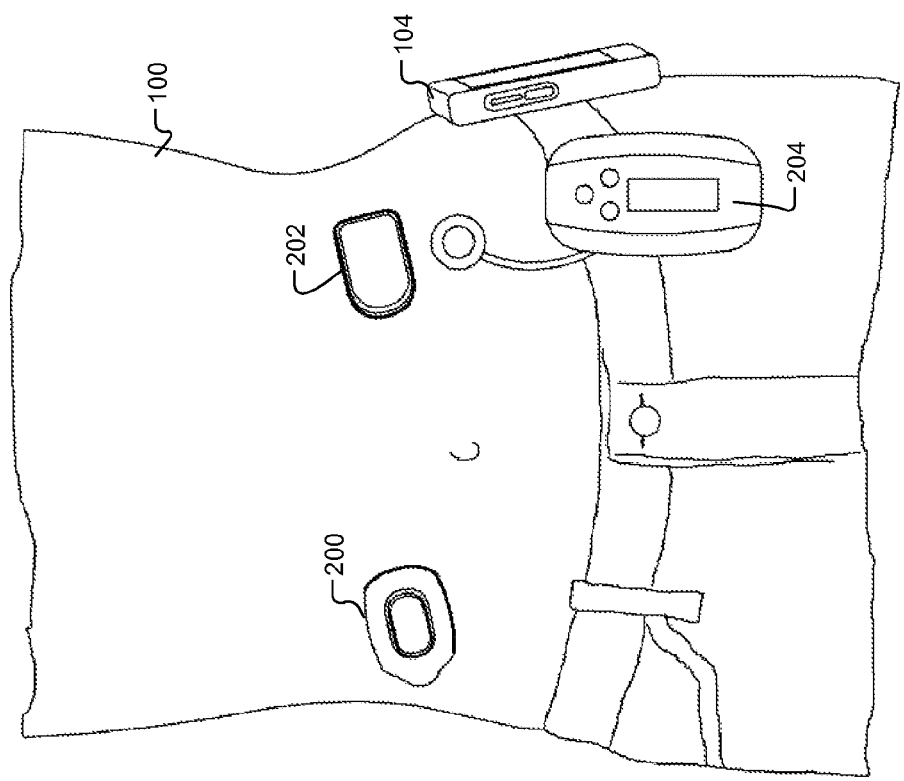
FIG. 1 shows a patient and a health care professional along with various devices that can be used to help the patient monitor and control health.

The following description is merely illustrative in nature and is in no way intended to limit the disclosure, its application, or uses. For purposes of clarity, the same reference numbers will be used in the drawings to identify similar elements. As used herein, the phrase at least one of A, B, and C should be construed to mean a logical (A or B or C), using a non-exclusive logical or. It should be understood that steps within a method can be executed in different order without altering the principles of the present disclosure.

As used herein, the term "module" can refer to, be part of, or include an Application Specific Integrated Circuit (ASIC); an electronic circuit; a combinational logic circuit; a field programmable gate array (FPGA); a processor (shared, dedicated, or group) that executes code; other suitable components that provide the described functionality; or a combination of some or all of the above, such as in a system-on-chip. The term "module" can include memory (shared, dedicated, or group) that stores code executed by the processor.

The term "code," as used above, can include software, firmware, and/or microcode, and can refer to programs, routines, functions, classes, and/or objects. The term "shared," as used above, means that some or all code from multiple modules can be executed using a single (shared) processor. In addition, some or all code from multiple modules can be stored by a single (shared) memory. The term "group," as used above, means that some or all code from a single module can be executed using a group of processors. In addition, some or all code from a single module can be stored using a group of memories.

The apparatuses and methods described herein can be implemented by one or more computer programs executed by one or more processors. The computer programs include processor-executable instructions that are stored on a non-transitory, tangible, computer readable medium. The computer programs can also include stored data. Examples of the non-transitory, tangible, computer readable medium include, but are not limited to, nonvolatile memory, magnetic storage, and optical storage.

A handheld blood glucose (bG) management device includes a processor that executes firmware for operating the diabetes management device. The firmware is stored in a firmware module that is implemented in a non-modifiable portion of memory of the diabetes management device. The firmware can be thought of as a routine executed by the processor to operate the diabetes management device.

One or more approvals of the firmware are typically necessary before the diabetes management device (executing the firmware) can be made publicly available. For example only, approval from one or more regulatory bodies (e.g., a Food and Drug Administration) can be required before the diabetes management device is made available in a region of the world that is subject to the regulations of the regulatory body. Before approving the firmware, a given regulatory body can require submission of a copy of the firmware, performance of one or more clinical tests to establish the operability of the firmware, and/or fulfillment of one or more other requirements.

Among other things, the firmware includes a subroutine for each different type of structured bG test that the diabetes management device is capable of performing. Each of the subroutines can be considered a submodule of the firmware module. One or more groups of bG samples are expected to be input for each structured bG test. One or more individual bG samples are expected to be input for each group of bG samples.

Entry criteria, adherence criteria, and exit criteria are associated with each structured bG test. Test configuration data is also associated with each structured bG test. Entry criteria, adherence criteria, and exit criteria are also associated with each expected bG sample group and each expected bG sample. The test configuration data may include how many data samples are expected to be input, how many data samples are expected for each group of data samples, spacing (e.g., period) between successive data samples, acceptance ranges or windows for each data sample, and/or other suitable data used in performing the structured bG test. Data collection for a structured bG test, for a group of bG samples, or for an individual bG sample can begin when the associated entry criteria are satisfied. A structured bG test, a group of bG samples, or a bG sample can be accepted as adhering to predetermined characteristics of the structured bG test, bG sample group, or bG sample when the associated adherence criteria are satisfied. Data collection for a structured bG test, a bG sample group, or a bG sample can end when the associated exit criteria are satisfied. Data collection for a structured bG test, a bG sample group, or a bG sample can alternatively end when the associated adherence criteria are satisfied.

All of the entry, adherence, and exit criteria could be written (coded) in the firmware in the firmware module (in the non-modifiable portion of memory). However, the requirement of regulatory approval of the firmware can limit the ability to modify/update one or more entry, adherence, and/or exit criteria if such modifications/updates are desired.

In the exemplary diabetes management device of the present disclosure, the entry, adherence, and exit criteria and the test configuration data can be stored in a modifiable portion of memory. In this manner, the test configuration data and/or entry, adherence, and/or exit criteria can be modified independently of the firmware. The firmware subroutines stored in the non-modifiable portion of memory point to where the associated test configuration data and the associated entry, adherence, and exit criteria are stored.

The separation in storage of the test configuration data and the entry, adherence, and entry criteria from the firmware module allows changes to the test configuration data and/or to the entry, adherence, and/or exit criteria to be made independently of the firmware. Therefore, because the firmware will not change when the test configuration data and/or entry, adherence, and/or exit criteria are changed/updated, another approval of the firmware can be unnecessary. Not having to obtain another approval can provide significant and measurable cost savings (e.g., from not having to conduct another round of clinical testing). This can also enable changes/updates to test configuration data and/or to entry, adherence, and/or exit criteria to be made publicly available sooner. Additionally, the same firmware can be distributed on diabetes management devices throughout the world while the test configuration data and/or the entry, adherence, and exit criteria can be updated remotely, for example, based on local standards.

Referring now to FIG. 1, a patient 100 with diabetes and a health care professional 102 are shown in a clinical environment. A person with diabetes can have a metabolic syndrome, pre-diabetes, type 1 diabetes, type 2 diabetes, gestational diabetes, etc. Healthcare providers for diabetes are diverse and include nurses, nurse practitioners, physicians, endocrinologists, and others and are collectively referred to as health care professionals.

During a health care consultation, the patient 100 typically shares with the health care professional 102 a variety of data including blood glucose (bG) measurements, continuous glucose monitor data, amounts and type of insulin administered, amounts of food and beverages consumed, exercise schedules, health status, and other lifestyle information. The health care professional 102 can obtain additional data for the patient 100, such as measurements of HbA1C, cholesterol levels, triglycerides, blood pressure, and weight. The data can be recorded manually or electronically on a handheld diabetes management device 104 (e.g., a handheld bG monitor device), a diabetes analysis software executed on a personal computer (PC) 106, and/or a web-based diabetes analysis site. The health care professional 102 can analyze the patient data manually or electronically using the diabetes analysis software and/or the web-based diabetes analysis site. After analyzing the data and reviewing how well the patient 100 followed a previously prescribed therapy, the health care professional 102 can decide whether to modify a therapy prescribed for the patient 100.

Figure 2:
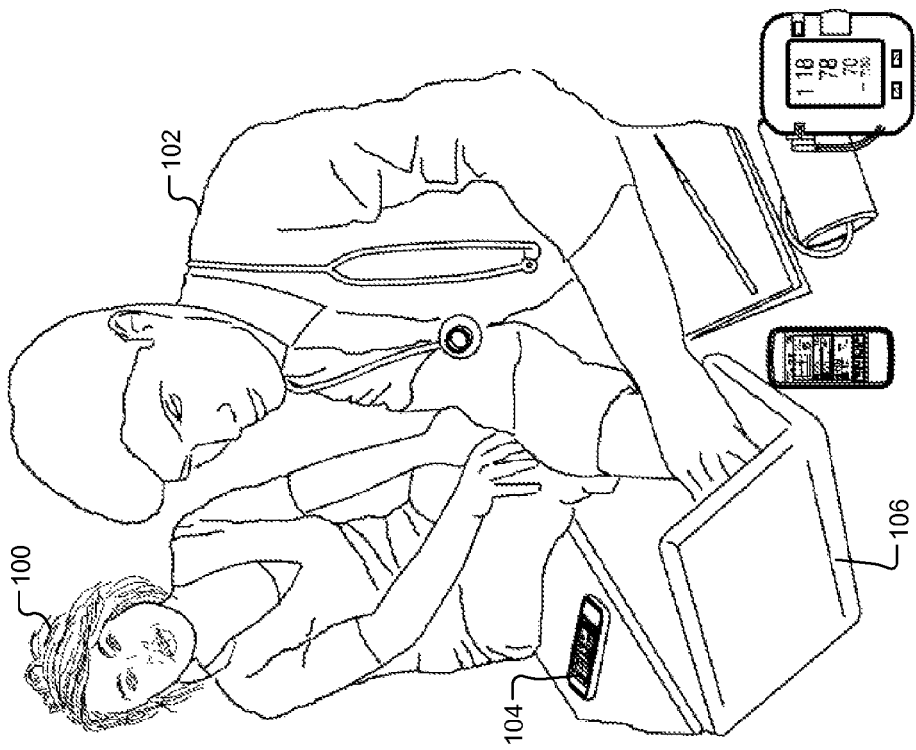
FIG. 2 shows a patient with a continuous glucose monitor (CGM), an ambulatory durable insulin infusion pump, an ambulatory non-durable insulin infusion pump, and a blood glucose (bG) management device.

Referring now to FIG. 2, the patient 100 can use a continuous glucose monitor (CGM) 200, an ambulatory durable insulin infusion pump 202 or an ambulatory non-durable insulin infusion pump 204 (collectively insulin pump 202 or 204), and the diabetes management device 104. The CGM 200 can use a subcutaneous sensor to sense and monitor the amount of glucose in the blood of the patient 100. The CGM 200 communicates bG measurements to the diabetes management device 104. The CGM 200 can also measure and communicate measurements to the diabetes management device 104 regarding insulin level in the blood of the patient 100.

The diabetes management device 104 performs various tasks including measuring and recording bG measurements, determining an amount of insulin to be administered to the patient 100 via the insulin pump 202 or 204, receiving user input via a user interface, archiving data, performing structured bG tests, etc. The diabetes management device 104 can transmit instructions to the insulin pump 202 or 204, and the insulin pump 202 or 204 selectively delivers insulin to the patient 100. Insulin can be delivered in the form of a meal bolus dose, a correction bolus dose, a basal dose, etc.

Figure 3:
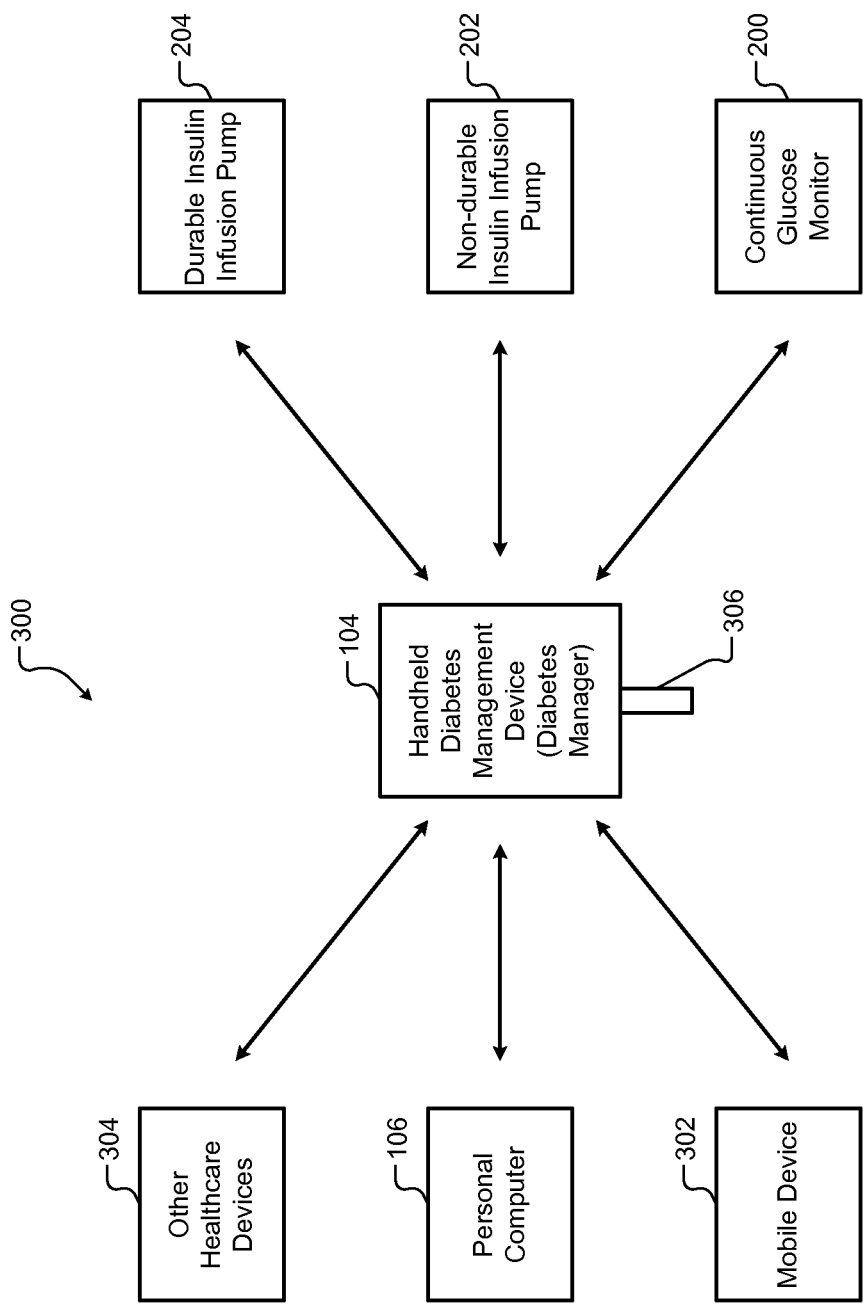
FIG. 3 shows a diabetes care system of systems that can be used to manage diabetes.

Referring now to FIG. 3, a diabetes management system 300 is shown which can be used by the patient 100 and/or the health care professional 102. The system 300 can include one or more of the following devices: the diabetes management device 104, the CGM 200, the insulin pump 202 or 204, a mobile device 302, the diabetes management software executed on the computer 106, and one or more other health care devices 304. The diabetes management device 104 can be configured as a system "hub" and communicate with one or more of the other devices of the system 300. The insulin pump 204, the mobile device 302, or another suitable device can alternatively serve as the system hub. Communication between various devices in the system 300 can be performed using wireless interfaces (e.g., Bluetooth) and/or wired interfaces (e.g., USB). Communication protocols used by these devices can include protocols compliant with the IEEE 11073 standard as extended using guidelines provided by Continua Health Alliance Design Guidelines. Further, health care records systems such as Microsoft HealthVault™ and Google Health™ can be used by the patient 100 and health care professional 102 to exchange information.

The diabetes management software running on the computer 106 can include an analyzer-configurator that stores configuration information for devices of the system 300. For example only, the configurator has a database to store configuration information for the diabetes management device 104 and the other devices. A user can interface the configurator through standard web based or computer graphical user interfaces (GUIs). The configurator selectively transmits user-approved configurations to the devices of the system 300. The analyzer selectively retrieves data from the devices of the system 300, stores the data in a database, selectively analyzes the data, and outputs analysis results through standard web based or computer GUIs.

Figure 4:
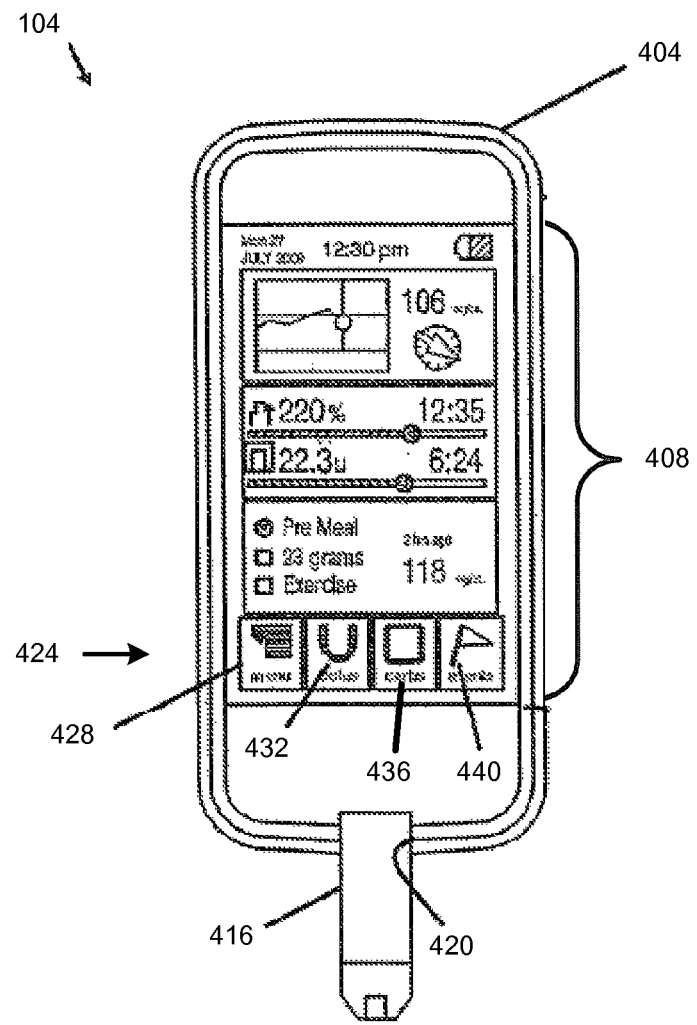
FIG. 4 is a high level diagram of an example implementation of a handheld diabetes management device.

Referring now to FIG. 4, a high level illustration of an example embodiment of the diabetes management device 104 is presented. The diabetes management device 104 includes, among other things, a housing 404, user unit control switches (not shown in FIG. 4), a touchscreen display 408, and a bG test strip port 420. The user unit control switches, for example, can include ON/OFF switches, volume switches, alarm switches for bG testing and/or insulin administration, and/or one or more other switches or other types of control devices that a user can use to control functions/operations of the diabetes management device 104.

A bG test strip 416 can be inserted into the bG test strip port 420. The bG test strip 416 can be inserted into the bG test strip port 420 by a user, from a test strip drum (not shown) located within the diabetes management device 104, or in another suitable manner. The bG test strip 416 is shown as being inserted into the bG test strip port 420 in the example of FIG. 4 and as separate from the bG test strip port 420 in the example of FIG. 5.

User selectable options 424 can be displayed on a portion of the display 408. The selectable options 424 can include a menu option 428, a bolus insulin option 432, a carbohydrate option 436, and an event option 440. One or more other user selectable options can additionally or alternatively be available. The user can access a device menu for the diabetes management device 104 by selecting the menu option 428. The user can input various insulin (and/or other medication) information (e.g., amount, insulin type, etc.) by selecting the bolus insulin option 432. The user can input various carbohydrate intake information (e.g., amount) by selecting the carbohydrate option 436. The user can also input other food intake information (e.g., protein content, fat content, etc.) by selecting the carbohydrate option 436. The user can input various event related information (e.g., meals, exercise, periods of stress, etc.) that can affect the user's bG measurements by selecting the event option 440.

Although the display 408 is described herein as a touchscreen display, the diabetes management device 104 can include another suitable form of display (e.g., LED, etc.). If a touchscreen display is not used, the user control switches can include specific buttons or controls by which the user is able to select various options and input markers needed to select, input, and perform "structured bG tests." "Structured bG tests" can also be referred to as "focused tests."

The above description is a broad description of the diabetes management device 104. In practice, the diabetes management device 104 can include additional controls, input ports, output ports, etc., as can be desired to further enhance its utility or its use with other components and devices (e.g., computers, infusion pumps, cellular phones, etc.). The description of the diabetes management device 104 should not be taken as limiting as to the construction of the diabetes management device 104 or as to the features and capabilities of the diabetes management device 104.

Figure 5:
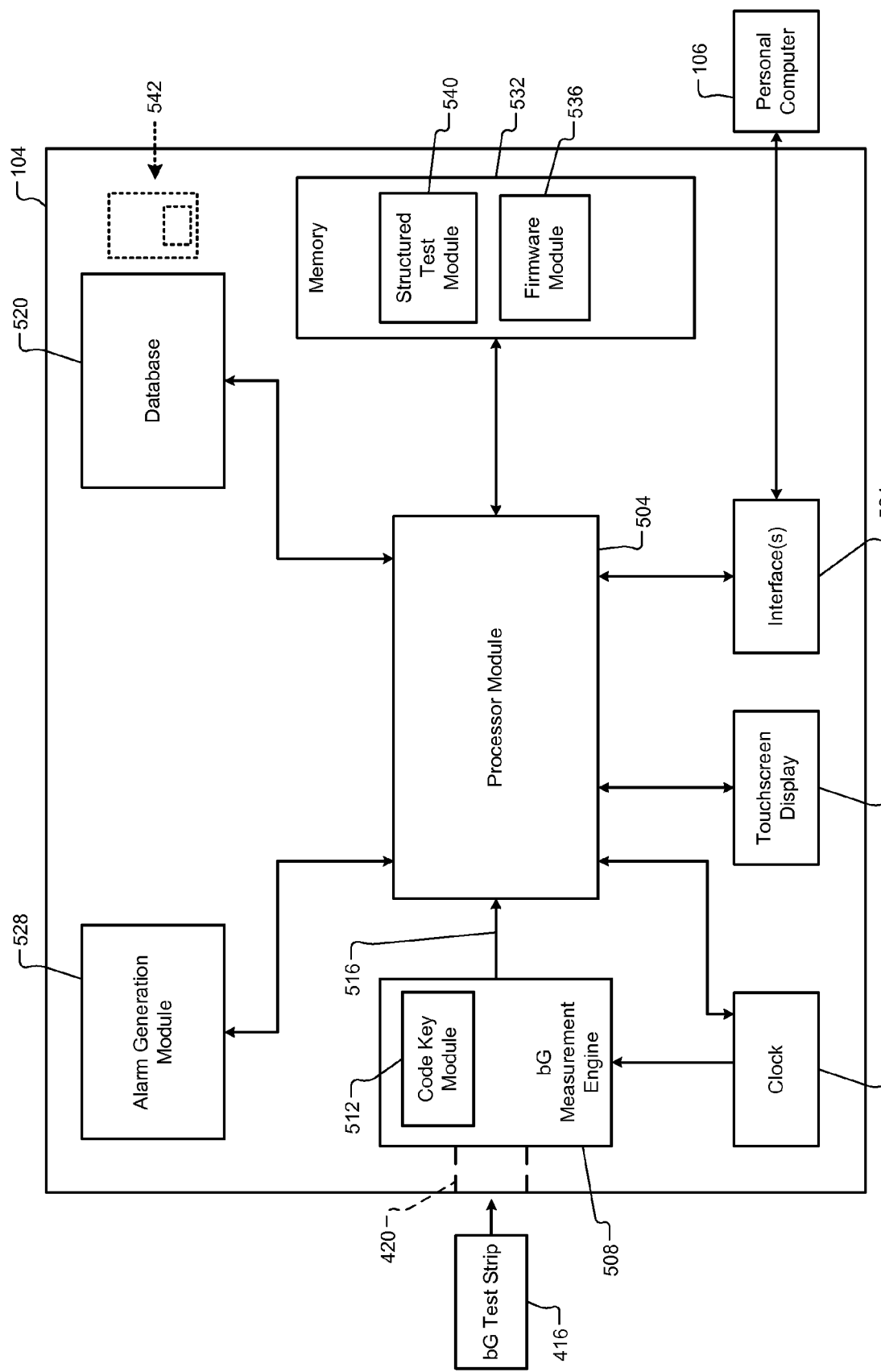
FIG. 5 includes a functional block diagram of an example implementation of the handheld diabetes management device.

Referring now to FIG. 5, a functional block diagram of the diabetes management device 104 is presented. The diabetes management device 104 can include a processor module (e.g., a microprocessor based subsystem) 504 that can receive information from a bG measurement engine 508. The bG measurement engine 508 can be located adjacent the bG test strip port 420.

The bG measurement engine 508 reads (measures) the bG test strip 416. The bG measurement engine 508 can include a code key module 512 that includes pre-calibrated data for determining a bG level from the bG test strip 416. The bG measurement engine 508 generates bG sample data 516 based on its reading of the bG test strip 416. Among other things, the bG sample data 516 includes data indicative of the bG level of a blood sample on the bG test strip 416. The processor module 504 can also receive bG sample data from other sources, such as via the CGM 200, the display 408, and/or another suitable source. The processor module 504 can receive user input data via, for example, the display 408 and/or one or more other suitable sources.

The bG measurement engine 508 can also generate the bG sample data 516 to indicate the date and time when the bG test strip 416 was read. In other words, the bG measurement engine 508 can include a time stamp with the bG sample data 516. In various implementations, the processor module 504 can selectively time stamp the bG sample data 516 and can time stamp user input data and other data when it is received.

A clock 518 can provide the date and time. The user can configure the present date and time, and the clock 518 thereafter tracks the present date and time. In various implementations, the present date and time can be acquired from (e.g., synchronized with) the computer 106. The bG measurement engine 508 communicates the bG sample data 516 to the processor module 504.

The processor module 504 is in communication with a database 520 used to store bG sample data, user input data, and other data. For example only, the processor module 504 can store each piece of bG sample data received in the database 520. The processor module 504 is also in communication with the display 408 and one or more interfaces 524. Each of the interfaces 524 can provide an interface between the diabetes management device 104 and an external device, such as the computer 106, the insulin pump 202 or 204, the CGM 200, the mobile device 302, the other health care devices 304, and/or one or more other suitable external devices.

The processor module 504 is also in communication with an alarm generation module 528. The alarm generation module 528 can generate one or more alarms when prompted by the processor module 504. For example only, the alarm generation module 528 can generate audible, tactile (e.g., vibratory), and/or visual alarms. The alarms can be used, for example, in prompting a user to input data for a structured bG test during a window of time around an acceptance time. The acceptance time may be a default time or set, for example, by the user.

The processor module 504 is also in communication with memory 532. For example only, the memory 532 can be NAND type flash memory or another suitable type of memory. While not shown in the example of FIG. 5, the database 520 can be implemented within the memory 532 in various implementations.

In an example embodiment, the structure of the memory 532 can be thought of as being modular, where the modules of the memory 532 each include a specific type of data. For example only, the memory 532 can include a firmware module 536 and a structured bG test module 540 as shown in the example of FIG. 5. The memory 532 can also include one or more other modules.

Firmware for the diabetes management device 104 is stored in the firmware module 536. In the case of the memory 532 being NAND type flash or another type of re-writable memory, the firmware module 536 is partitioned from other portions of the memory 532 and otherwise made non-modifiable (e.g., read only). In this manner, the firmware cannot be updated, re-written, or otherwise modified, via user input to the diabetes management device 104 or otherwise. In various implementations, the firmware module 536 can be implemented independently of the memory 532, such as within read only memory (ROM) or another suitable type of memory as shown in dashed lines at 542. In all implementations, however, the firmware module 536 is or is made non-modifiable.

The processor module 504 selectively executes one or more portions of the firmware to perform various functions of the diabetes management device 104. For example only, the processor module 504 can execute a portion of the firmware corresponding to a structured bG test when performance of the structured bG test is initiated. For example only, the user, a health care professional, or the device itself can initiate performance of the structured bG test. While not specifically stated, the actions performed by the processor module 504 described below can be performed in executing the firmware for the structured bG test.

The processor module 504 can create a table in the database 520 with one or more entries for each bG sample and group of bG samples that is expected to be input for the structured bG test. The processor module 504 can selectively trigger generation of one or more alarms and/or cause one or more reminders indicating that user input or a bG sample is expected for the structured bG test to be displayed on the display 408. The processor module 504 may limit the number of structured bG tests that are being performed on the diabetes management device 104 at a given time to one.

All of the entry, adherence, and exit criteria used in executing the structured bG tests are stored in the structured bG test module 540. Test configuration data used in executing the structured bG tests is also stored in the structured bG test module 540. Importantly, unlike the firmware stored in the firmware module 536, the structured bG test module 540 is modifiable and remotely updatable. For example only, one or more entry, adherence, and/or exit criteria and/or test configuration data can be remotely updated or otherwise modified via the software executed on the computer 106 or in another suitable manner. This is advantageous as it allows the ready modification of such criteria and/or test configuration data in the future should such modification be necessary, preferable, etc. An additional significant advantage is that since the firmware module 536 is non-modifiable, a future modification of entry, adherence, and/or exit criteria and/or the test configuration data will not trigger the need for another process of regulatory approval by the manufacturer of the diabetes management device 104.

The portion of the firmware that the processor module 504 executes to perform a given structured bG test points to associated test configuration data, entry, adherence, and exit criteria stored in the structured bG test module 540. The processor module 504 selectively retrieves the associated test configuration data and the associated entry, adherence, and exit criteria from the structured bG test module 540. The processor module 504 can retrieve all of the test configuration data and the entry, adherence, and exit criteria associated with the structured bG test when performance of the structured bG test is initiated, as necessary during execution of the structured bG test, or in another suitable manner. The processor module 504 can retrieve entry, adherence, and exit criteria for each expected bG sample, for each expected group of bG samples (i.e., sample groups), and for the structured bG test. For example only, the test configuration data may include data regarding a number of data samples expected to be input for the structured bG test, a number of data sample groups for the bG structured test, an expected spacing (e.g., period) between successive data samples, a period (e.g., number of days) over which the structured bG test is to be conducted, an acceptance range or window of time for each data sample, and/or other suitable data.

The entry criteria for an expected (individual) bG sample include one or more criterion used in determining whether to begin expecting receipt of bG sample data. For example only, the entry criteria can include a time (of a date) after which the bG sample is expected to be input. For example only, if a given bG sample is expected on a given date between time X and time Y, the entry criteria for the bG sample can include the date and time X. The entry criteria for a bG sample can additionally or alternatively include one or more other suitable criteria, such as user input data, whether user input data has been received, whether the user input data exhibits predetermined characteristics, whether an earlier input satisfied its associated adherence criteria, etc.

The adherence criteria for a received bG sample include one or more criterion used in determining whether to accept or reject the bG sample. In other words, the adherence criteria for a received bG sample include criteria used in determining whether the bG sample data is acceptable for consideration in making a medical determination. For example only, if a bG sample is expected on a given date between time X and time Y, the adherence criteria for the bG sample can include the date and a window of time defined by time X and time Y. Accepted bG samples can be marked for consideration in making the medical determination. Rejected bG samples can be determining whether exit criteria for a bG sample group and/or the structured bG test are satisfied.

The processor module 504 selectively accepts or rejects received bG samples based on comparisons of one or more characteristics of the bG sample data with the associated adherence criteria. For example only, the processor module 504 can mark a received bG sample as accepted when the associated adherence criteria are satisfied. Conversely, the processor module 504 can mark the bG sample as rejected when a received bG sample does not satisfy the associated adherence criteria.

The exit criteria for an expected bG sample include one or more criterion used in determining whether to stop expecting the input of an expected bG sample. For example only, the exit criteria for a bG sample can include satisfaction of the adherence criteria associated with the bG sample, satisfaction of the exit criteria for a bG sample group of which the expected bG sample is a part, and/or satisfaction of the exit criteria for the structured bG test. The exit criteria for an expected bG sample can additionally or alternatively include an ending time and date. For example only, if a bG sample is expected on a given date between time X and time Y, the exit criteria for the bG sample can include the date and time Y. The exit criteria can also include whether a previous bG sample satisfied its adherence criteria, and/or one or more other suitable exit criteria.

The processor module 504 can selectively mark an expected bG sample of the structured bG test as having been missed (or otherwise not received) in the database 520 when the exit criteria for the bG sample are satisfied and the satisfaction is not due to the associated adherence criteria being satisfied. For example only, if a bG sample is expected on a given date between time X and time Y, the processor module 504 can mark the bG sample as having been missed in the database 520 when a bG sample is not received and time Y passes.

The entry criteria for an expected bG sample group includes one or more criterion used in determining whether to begin expecting that bG samples of the bG sample group will be input. For example only, the entry criteria can include a time (of a date) after which the one or more bG samples of the bG sample group are expected to be input. For example only, if the bG sample(s) of a bG sample group are expected to be input beginning on a given date, the entry criteria for the given sample group can include the date. The entry criteria for an expected sample group can additionally or alternatively include one or more other suitable criteria.

The adherence criteria for an expected bG sample group include one or more criterion used in determining whether to accept or reject the bG sample group (including accepted bG samples of the bG sample group). In other words, the adherence criteria for a bG sample group includes criteria used in determining whether the bG samples of the bG sample group as a whole are acceptable for consideration in making the medical determination. For example only, the adherence criteria for an expected sample group can include a threshold number of accepted bG samples. For example only, if X bG samples are expected to be input for a given bG sample group and Y of the X bG samples are expected to be accepted, Y can be adherence criteria for the bG sample group. X and Y are integers, and Y is greater than zero and less than or equal to X. The adherence criteria for an expected bG sample group can additionally or alternatively include one or more other suitable criteria.

The processor module 504 selectively accepts or rejects bG sample groups based on comparisons of one or more characteristics of the bG sample groups with the associated adherence criteria. For example only, the processor module 504 can mark a bG sample group as accepted when the associated adherence criteria are satisfied.

The exit criteria for a bG sample group includes one or more criterion used in determining the expectation of receipt of expected bG samples for the bG sample group should end. For example only, the exit criteria for a bG sample group can include satisfaction of the adherence criteria associated with the bG sample group and/or satisfaction of exit criteria for the structured bG test. The exit criteria for a bG sample group can additionally or alternatively include an ending date and time for the sample group. For example only, if all of the bG samples of a bG sample group are expected to be input before a given date, the exit criteria for the bG sample group can include the given date. The exit criteria for a bG sample group can additionally or alternatively include a threshold number of missed or rejected bG samples. For example only, if X bG samples are expected for a bG sample group and Y of the X bG samples is a maximum number of the expected bG samples that can be missed or rejected, Y can be exit criteria for the bG sample group. X and Y are integers, and Y is greater than or equal to zero and less than or equal to X. The exit criteria for a bG sample group can additionally or alternatively include one or more other suitable criteria.

The entry criteria for the structured bG test include one or more criterion used in determining whether to begin performing the structured bG test. For example only, the entry criteria for the structured bG test can include a time (of a date) after which the structured bG test is to begin. The entry criteria for the structured bG test can additionally or alternatively include a threshold age of the user, a threshold range for HbA1c of the user, a threshold length of time that the user has had diabetes, a specified type of diabetes diagnosed to the user, a threshold body mass index (BMI) of the user, and/or a threshold fasting plasma glucose level. The entry criteria for the structured bG test can additionally or alternatively include one or more other suitable criteria.

The adherence criteria for the structured bG test includes one or more criterion used in determining whether to accept or reject all of the bG data received for the structured bG test. In other words, the adherence criteria for the structured bG test includes criteria used in determining whether accepted groups of bG samples, taken as a whole, are acceptable for consideration in making the medical determination. For example only, the adherence criteria for the structured bG test can include a threshold number of accepted bG sample groups. For example only, if X bG sample groups are expected for the structured bG test and Y of the X bG sample groups is a minimum number of the bG sample groups to be accepted, Y can be adherence criteria for the structured bG test. X and Y are integers, and Y is greater than zero and less than or equal to X. The adherence criteria for the structured bG test can additionally or alternatively include one or more other suitable criteria.

The processor module 504 selectively accepts or rejects the sample data input for the structured bG test based on one or more characteristics of the bG sample groups or the bG samples and the associated adherence criteria. For example only, the processor module 504 can mark the structured bG test as accepted when the associated adherence criteria are satisfied.

The exit criteria for the structured bG test include one or more criterion used in determining the expectation of receipt of bG samples for the structured bG test should end. For example only, the exit criteria for the structured bG test can include satisfaction of the adherence criteria associated with the structured bG test. The exit criteria for the structured bG test can additionally or alternatively include an ending date (and possibly time) for the structured bG test. For example only, if all of the samples of the structured bG test are expected to be input before a given date, the exit criteria for the structured bG test can include the date. The exit criteria for the structured bG test can additionally or alternatively include a threshold number of missed and rejected bG samples and/or a threshold number of rejected bG sample groups. For example only, if X bG samples are expected for a sample group, and if Y of the X bG samples is a maximum number of the expected bG samples that can be missed or rejected, Y can be exit criteria for the structured bG test. X and Y are integers, and Y is greater than or equal to zero and less than or equal to X. For another example only, if X bG sample groups are expected for the structured bG test and Y of the X bG sample groups is a maximum number of the bG sample groups that can be rejected, Y can be exit criteria for the structured bG test. X and Y are integers, and Y is greater than or equal to zero and less than or equal to X. The exit criteria for a bG sample group can additionally or alternatively include one or more other suitable criteria.

Further information on adherence, exit, and entry criteria can be found in paragraphs [0048] and [0092]-[0116] of commonly assigned U.S. patent application Ser. No. 12/643,338, filed Dec. 21, 2009, and titled "Structured Testing Method for Diagnostic or Therapy Support of a Patient with a Chronic Disease and Devices Thereof." Additional information on adherence, exit, and entry criteria can also be found in paragraphs [0087]-[0112] of commonly assigned U.S. patent application Ser. No. 12/643,415, filed on Dec. 21, 2009, and titled "Management Method and System for Implementation, Execution, Data Collection, and Data Analysis of a Structured Collection Procedure Which Runs on a Collection Device." The above patent applications, including the above mentioned paragraphs, are incorporated by reference.

Figure 6:
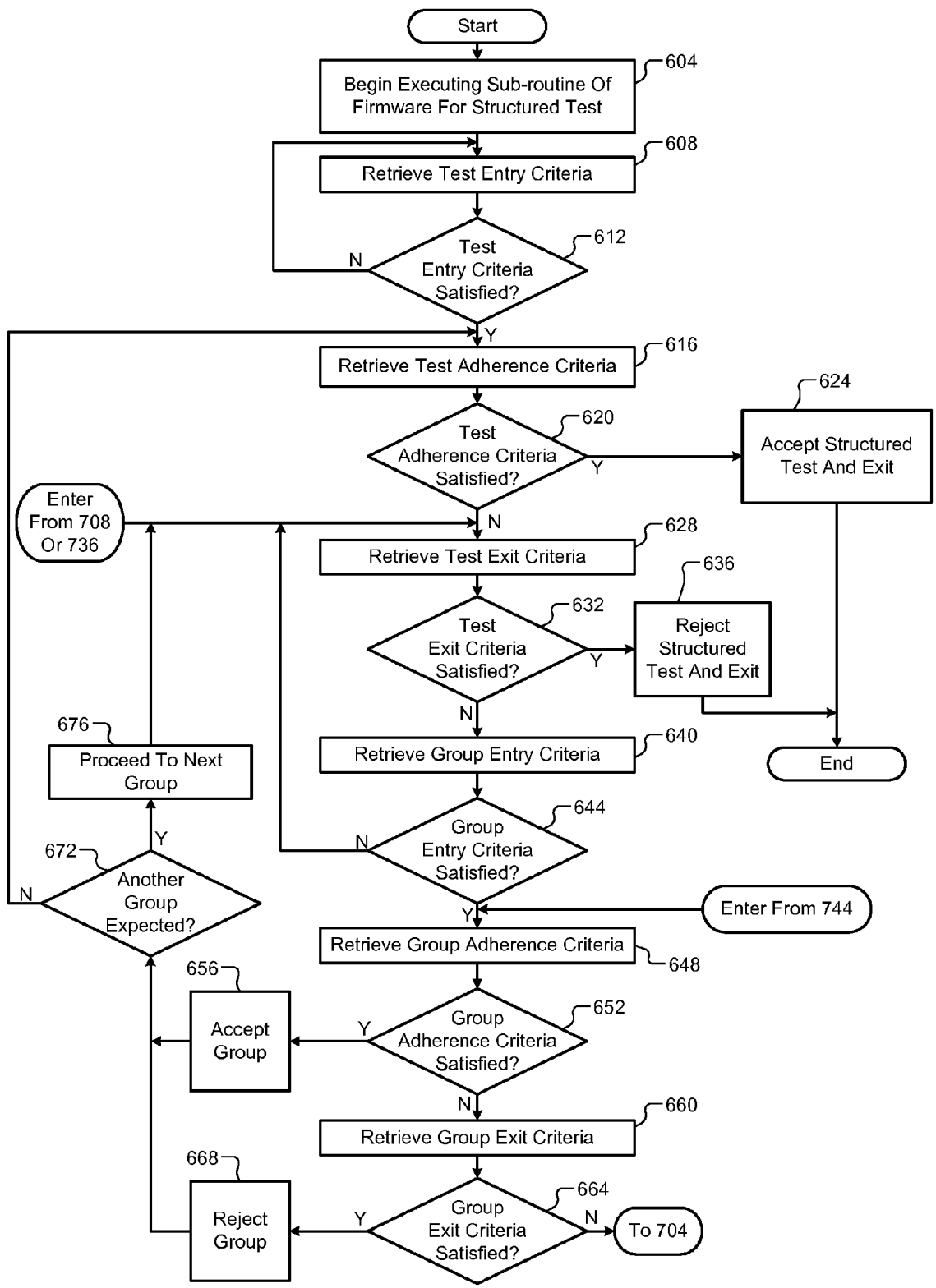
FIGS. 6-7 include a flowchart depicting an example method of performing a structured bG test on the handheld diabetes management device.
Figure 7:
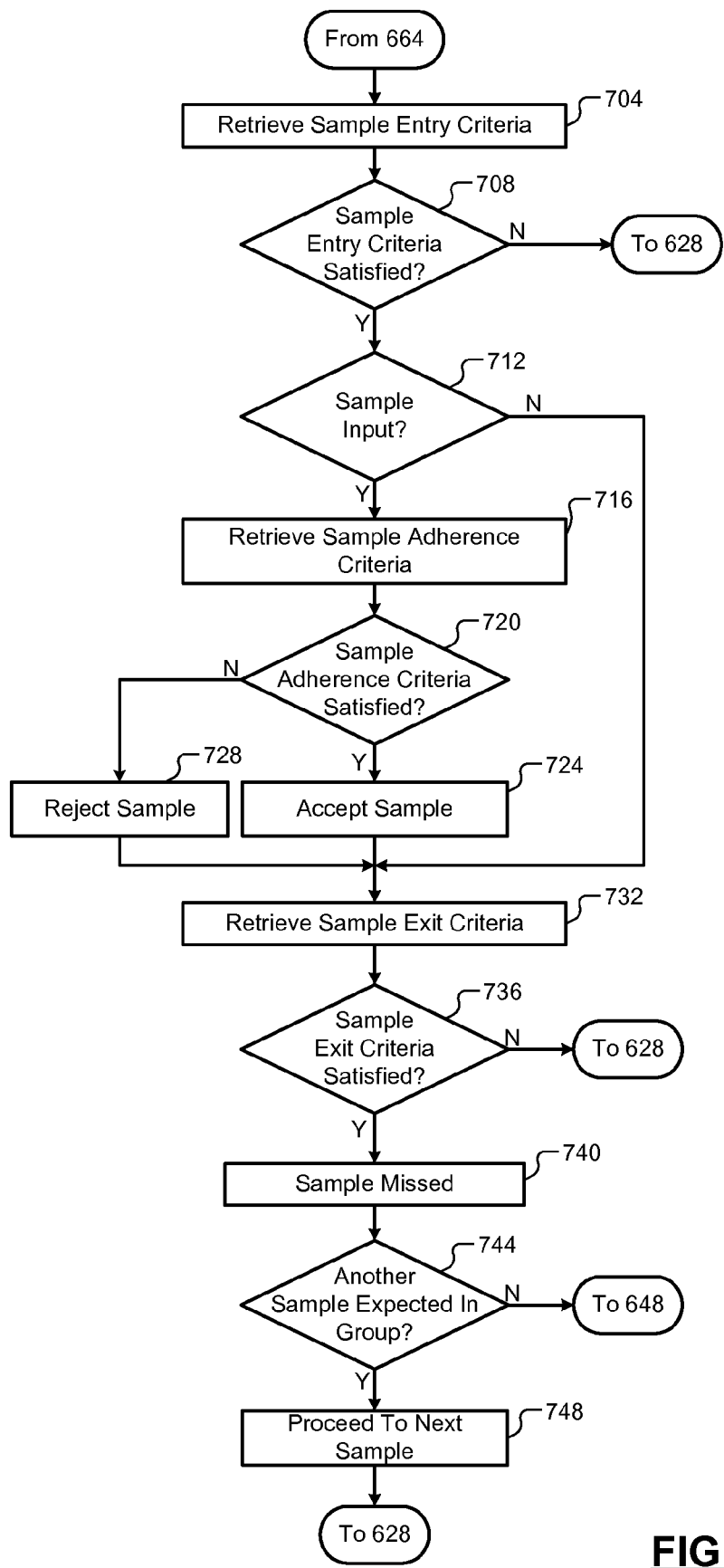

Referring now to FIGS. 6-7, an example method that the processor module 504 can execute in carrying out the firmware for a given structured bG test is presented. Control can begin with operation 604 where execution of the sub-routine of the firmware for the structured bG test can begin. The sub-routine and the firmware are stored in a non-modifiable portion of memory of the diabetes management device 104.

At operation 608, the entry criteria for the structured bG test can be retrieved from a modifiable portion of memory of the diabetes management device 104. A determination can be made as to whether the entry criteria for the structured bG test are satisfied at operation 612. If true, operation 616 can be performed; if false, operation 608 can be returned to. At operation 616, the adherence criteria for the structured bG test can be retrieved from the modifiable portion of memory.

At 620, a determination can be made as to whether the adherence criteria for the structured bG test are satisfied. If true, the structured bG test can be accepted and performance of the structured bG test can be exited at operation 624. If false, operation 628 can be performed. The exit criteria for the structured bG test can be retrieved from the modifiable portion of memory at operation 628. A determination can be made at operation 632 as to whether the exit criteria for the structured bG test are satisfied. If true, the structured bG test can be rejected and performance of the structured bG test can be exited at operation 636. If false, operation 640 can be performed.

The entry criteria for a bG sample group can be retrieved from the modifiable portion of memory at operation 640. A determination can be made as to whether the entry criteria for the bG sample group are satisfied at operation 644. If true, operation 648 can be performed; if false, operation 628 can be returned to. At operation 648, the adherence criteria for the bG sample group can be retrieved from the modifiable portion of memory. A determination can be made as to whether the adherence criteria for the bG sample group are satisfied at operation 652. If true, the bG sample group can be accepted at operation 656 and operation 672 can be performed, which is discussed in detail below. If false, operation 660 can be performed.

At operation 660, the exit criteria for the bG sample group can be retrieved from the modifiable portion of memory. A determination can be made as to whether the exit criteria for the bG sample group are satisfied at operation 664. If true, the bG sample group can be rejected at 668 and operation 672 can be performed. If false, operation 704 of FIG. 7 can be performed. At operation 672, a determination can be made as to whether another bG sample group is expected for the structured bG test. If true, the next bG sample group can be proceeded to at operation 676 and operation 628 can be returned to. If false, operation 616 can be returned to.

Referring now to FIG. 7, the entry criteria for an expected bG sample can be retrieved from the modifiable portion of memory at operation 704. A determination can be made as to whether the entry criteria for the bG sample are satisfied at operation 708. If true, operation 712 can be performed; if false, operation 628 can be returned to. A determination can be made as to whether the expected bG sample has been input at operation 712. If true, operation 716 can be performed; if false, operation 732 can be performed, which is discussed further below.

The adherence criteria for the bG sample can be retrieved from the modifiable portion of memory at operation 716. A determination can be made as to whether the adherence criteria for the bG sample are satisfied at operation 720. If true, the bG sample can be accepted at operation 724 and operation 732 can be performed; if false, the bG sample can be accepted at operation 728 and operation 732 can be performed. At operation 732, the exit criteria for the bG sample can be retrieved from the modifiable portion of memory.

A determination can be made as to whether the exit criteria for the bG sample are satisfied at operation 736. If true, the bG sample can be marked as having been missed at operation 740 and operation 744 can be performed; if false, operation 628 can be returned to. At operation 744, a determination can be made as to whether another bG sample is expected for the bG sample group. If true, the next bG sample can be proceeded to at operation 748 and operation 628 can be returned to; if false, operation 648 can be returned to.

A handheld diabetes management device having improved updatability of entry, adherence, and exit criteria, comprises: a blood glucose (bG) management engine, memory, a display, and a processor module. The bG measurement engine that measures a bG level in a sample of blood of a user and that generates sample data indicative of the bG level. The processor module is in communication with the bG measurement engine, the display, and the memory. The processor module selectively executes firmware stored in a non-modifiable portion of the memory for performing operations to carry out a structured bG test; selectively retrieves entry, adherence, and exit criteria stored in a modifiable portion of the memory for individual bG samples expected to be input for the structured bG test; selectively retrieves entry, adherence, and exit criteria stored in the modifiable portion of the memory for bG sample groups expected for the structured bG test; and retrieves entry, adherence criteria, and exit criteria from the modifiable portion of the memory for the structured bG test.

In other features, the processor module of the handheld diabetes management device begins collection of data for the structured bG test when the entry criteria for the structured bG test are satisfied.

In still other features the processor module of the handheld diabetes management device ends data collection for the structured bG test when the adherence criteria or the exit criteria for the structured bG test are satisfied.

In further features, the processor module of the handheld diabetes management device marks data stored for the structured bG test as accepted when the adherence criteria for the structured bG test are satisfied.

In still further features, the processor module of the handheld diabetes management device begins collection of data for a bG sample group when the entry criteria for the bG sample group are satisfied.

In other features, the processor module of the handheld diabetes management device ends data collection for a bG sample group of the structured bG test when one of the adherence criteria and the exit criteria for the bG sample group are satisfied.

In still other features, the non-modifiable portion of the firmware is partitioned from other portions of the memory and marked as being non-modifiable.

In further features, the non-modifiable portion of memory is implemented in a first memory module, the modifiable portion of memory is implemented in a second memory module, and the first and second memory modules are separate memory modules.

In still further features, a diabetes management system includes the handheld diabetes management device of claim 1; and a computer that is remote to the handheld diabetes management device. The computer selectively updates at least one of the entry, adherence, and exit criteria.

Another handheld diabetes management device having improved updatability of entry, adherence, and exit criteria, comprises a blood glucose (bG) management engine, memory, a display, and a processor module. The bG measurement engine that measures a bG level in a sample of blood of a user and that generates sample data indicative of the bG level. The processor module is in communication with the bG measurement engine, the display, and the memory. The processor module selectively executes firmware for performing operations to carry out a structured bG test stored in a non-modifiable portion of the memory and selectively retrieves entry, adherence, and exit criteria for the structured bG test stored a modifiable portion of the memory.

In other features, the processor module begins collection of data for the structured bG test when the entry criteria are satisfied.

In still other features, the processor module ends data collection for the structured bG test when the adherence criteria or the exit criteria for the structured bG test are satisfied.

In further features, the non-modifiable portion of the firmware is partitioned from other portions of the memory and marked as being non-modifiable.

In still further features, the non-modifiable portion of memory is implemented in a first memory module, the modifiable portion of memory is implemented in a second memory module, and the first and second memory modules are separate memory modules.

A computer readable storage medium for a handheld blood glucose (bG) management device that measures a user's bG level and that includes a touchscreen display, the computer readable storage medium comprising a modifiable portion and a non-modifiable portion. The modifiable portion includes adherence, exit, and entry criteria for performing a structured bG test are stored. The non-modifiable portion includes firmware that, when executed by a processor of the handheld diabetes management device, causes the processor to perform the structured bG test involving obtaining measurements of the user's bG level according to a predefined schedule and selectively retrieving the adherence, exit, and entry criteria from the modifiable portion.

A method of improving updatability of entry, adherence, and exit criteria stored in memory of a handheld diabetes management device, the method comprises: providing the handheld diabetes management device with a blood glucose (bG) measurement engine that measures a bG level in a sample of blood of a user and that generates sample data indicative of the bG level; providing the handheld diabetes management device with the memory and a touchscreen display; providing the handheld diabetes management device with a processor module that is in communication with the bG measurement engine, the touchscreen display, and the memory; storing firmware that is executable by the processor module for performing operations to carry out a structured bG test in a non-modifiable portion of the memory; and storing the entry, adherence, and exit criteria in a modifiable portion of the memory.

In other features, the storing the entry, adherence, and exit criteria comprises: storing entry, adherence, and exit criteria stored for individual bG samples expected to be input in the carrying out of the structured bG test in the modifiable portion of the memory; storing entry, adherence, and exit criteria for groups of the individual bG samples expected in the carrying out of the structured bG test; and storing entry, adherence criteria, and exit criteria for the structured bG test in the modifiable portion of the memory.

In still other features, the method further comprises partitioning the non-modifiable portion of the firmware from other portions of the memory and marking the firmware as being non-modifiable.

The broad teachings of the disclosure can be implemented in a variety of forms. Therefore, while this disclosure includes particular examples, the true scope of the disclosure should not be so limited since other modifications will become apparent to the skilled practitioner upon a study of the drawings, the specification, and the following claims.

What is claimed is:

1. A handheld diabetes management device having improved updatability of entry, adherence, and exit criteria, the handheld diabetes management device comprising:
    a blood glucose (bG) measurement engine that measures a bG level in a sample of blood of a user and that generates sample data indicative of the bG level;
    memory;
    a display; and
    a processor module, in communication with the bG measurement engine, the display, and the memory, that:
        selectively executes firmware having regulatory approval stored in a non-modifiable portion of the memory for performing operations to carry out a structured bG test;
        selectively retrieves sample entry, sample adherence, and sample exit criteria stored in a modifiable portion of the memory for individual bG samples expected to be input for the structured bG test;
        selectively retrieves group entry, group adherence, and group exit criteria stored in the modifiable portion of the memory for bG sample groups expected for the structured bG test; and
        selectively retrieves test entry, test adherence, and test exit criteria from the modifiable portion of the memory for the structured bG test,
        wherein the group entry, group adherence, and group exit criteria are different than the sample entry, sample adherence, and sample exit criteria, and
        wherein the test entry, test adherence, and test exit criteria are different than the group entry, group adherence, and group exit criteria and the sample entry, sample adherence, and sample exit criteria.

2. The handheld diabetes management device of claim 1 wherein the processor module begins collection of data for the structured bG test when the test entry criteria for the structured bG test are satisfied.

3. The handheld diabetes management device of claim 1 wherein the processor module ends data collection for the structured bG test when the test adherence criteria or the test exit criteria for the structured bG test are satisfied.

4. The handheld diabetes management device of claim 3 wherein the processor module marks data stored for the structured bG test as accepted when the test adherence criteria for the structured bG test are satisfied.

5. The handheld diabetes management device of claim 1 wherein the processor module begins collection of data for a bG sample group when the group entry criteria for the bG sample group are satisfied.

6. The handheld diabetes management device of claim 1 wherein the processor module ends data collection for a bG sample group of the structured bG test when one of the group adherence criteria and the group exit criteria for the bG sample group are satisfied.

7. The handheld diabetes management device of claim 1 wherein the non-modifiable portion of the memory is partitioned from other portions of the memory and marked as being non-modifiable.

8. The handheld diabetes management device of claim 1 wherein the non-modifiable portion of memory is implemented in a first memory module,
   wherein the modifiable portion of memory is implemented in a second memory module, and
   wherein the first and second memory modules are separate memory modules.

9. A diabetes management system comprising:
   the handheld diabetes management device of claim 1; and
   a computer that is remote to the handheld diabetes management device and that selectively updates at least one of the sample entry, sample adherence, sample exit, group entry, group adherence, group exit, test entry, test adherence, and test exit criteria.

* * * * *